United States Patent [19]
Tzu et al.

[11] Patent Number: 6,018,392
[45] Date of Patent: Jan. 25, 2000

[54] APPARATUS AND METHOD FOR INSPECTING PHASE SHIFTING MASKS

[75] Inventors: San-De Tzu; Shy-Jay Lin, both of Taipei, Taiwan

[73] Assignee: Taiwan Semiconductor Manufacturing Company, Hsin-Chu, Taiwan

[21] Appl. No.: 09/177,340

[22] Filed: Oct. 23, 1998

[51] Int. Cl.[7] .................................................. G01B 9/02
[52] U.S. Cl. .......................... 356/351; 356/361; 356/357
[58] Field of Search ..................................... 356/357, 351, 356/361

[56] References Cited

U.S. PATENT DOCUMENTS

| | | | |
|---|---|---|---|
| 5,270,796 | 12/1993 | Tokui et al. | 356/394 |
| 5,353,116 | 10/1994 | Tanigawa et al. | 356/390 |
| 5,379,348 | 1/1995 | Watanabe et al. | 382/8 |
| 5,446,540 | 8/1995 | Lin | 356/345 |
| 5,482,799 | 1/1996 | Isao et al. | 430/5 |
| 5,677,092 | 10/1997 | Takekuma et al. | 430/30 |

*Primary Examiner*—Robert H. Kim
*Assistant Examiner*—Andrew H. Lee
*Attorney, Agent, or Firm*—George O. Saile; Stephen B. Ackerman; Larry J. Prescott

[57] ABSTRACT

An apparatus for die to die inspection of masks having transparent phase shifting elements and a method of die to die inspection of masks having transparent phase shifting elements. Light from a light source is directed through a transparent mask substrate and a phase shifting mask element to a first objective lens, and through the transparent mask substrate and another phase shifting mask element to a second objective lens. Light from the first objective lens is then given a 180° phase shift by a phase adjustment unit. Light from the phase adjustment unit and the second objective lens is combined at a split mirror and directed to a detector. The method makes use of the fact that the intensity of the light at the detector is proportional to the square of the cosine of one half of the phase angle between the light from the phase adjusting unit and light from the second objective lens. If the intensity of light reaching the detector is not zero, or very small, the mask has a defect.

24 Claims, 4 Drawing Sheets

APPARATUS AND METHOD FOR INSPECTING PHASE SHIFTING MASKS

BACKGROUND OF THE INVENTION (1) Field of the Invention

This invention relates to an apparatus and a method for inspecting masks which comprise transparent phase shifting mask elements.

(2) Description of the Related Art

Inspection of phase shifting mask elements is a problem because defects are not readily apparent in the transparent phase shifting material.

U.S. Pat. No. 5,270,796 to Tokui et al. describes an apparatus for inspecting a phase shift mask using a phase difference detector and a reference signal. The reference signal is generated from another mask having the same pattern or from CAD data.

U.S. Pat. No. 5,353,116 to Tanigawa et al. describes a defect inspection system which projects two pattern images from two neighboring dies on the phase shift mask. The two images are superimposed and compared.

U.S. Pat. No. 5,379,348 to Watanabe et al. describes a pattern defects inspection system for phase shifting masks.

U.S. Pat. No. 5,446,540 to Lin describes a method of inspecting phase shift masks using phase-error enhancing.

U.S. Pat. No. 5,482,799 to Isao et al. describes a phase shifting mask and a method of manufacturing the phase shifting mask.

U.S. Pat. No. 5,677,092 to Takekuma et al. describes a method of fabricating a phase shifting mask and a method of inspecting the masks.

SUMMARY OF THE INVENTION

Masks formed using phase shifting materials find frequent use in photolithographic processing of integrated circuit wafers. As feature sizes have become smaller the masks used in photolithographic processing have made increasing use of phase shifting materials to improve image definition and depth of focus.

The phase shifting materials used in mask fabrication provide a phase shift for light passing through the phase shifting materials relative to light which does not pass through the phase shifting materials, but are otherwise transparent. The amount of phase shift provided to the light depends not only on the materials used but on the thickness of the materials. This transparent nature of the phase shifting materials makes inspection of the masks extremely difficult. Variations in thickness as well as other defects are difficult to detect. Defects in the masks will lead to defects in the integrated circuits fabricated using the masks.

FIG. 1 shows a cross section of a binary mask having a transparent mask substrate 10 and opaque mask elements 12. Since the mask elements in the binary mask are opaque they are relatively easy to inspect.

FIG. 2A shows a cross section of a Levenson type phase shifting mask having a transparent mask substrate 10, opaque mask elements 12, and transparent phase shifting mask elements 14. Since the phase shifting mask elements 14 are transparent they are much more difficult to inspect for defects. FIG. 2B shows a mask 11 having a transparent mask substrate 11 and a number of die positions. FIG. 2B shows a first die position 61 and a second die position 62.

It is a principle objective of this invention to provide an apparatus for inspecting masks utilizing phase shifting material which will easily detect defects in transparent phase shifting material.

It is another principle objective of this invention to provide a method of inspecting masks utilizing phase shifting material which will easily detect defects in transparent phase shifting material.

These objectives are achieved with an apparatus used for die to die inspection of masks having phase shifting material in the mask. The apparatus is used for die to die inspection of masks having a number of identical die images at different positions on the same transparent mask substrate. The apparatus comprises a light source, a first objective lens, a first condenser lens, a second objective lens, a second condenser lens, a phase adjustment unit, and a split mirror. A mask is positioned so that a first die position is placed between the first objective lens and the first condenser lens and a second die position is placed between the second objective lens and the second condenser lens. Light from the light source illuminates both the first condenser lens and the second condenser lens. Light illuminating the first objective lens first passes through the first condenser lens. Light illuminating the second objective lens first passes through the second condenser lens. The phase adjustment unit is adjusted to provide a 180° phase shift to the light exiting the first objective lens relative to the light exiting the second objective lens.

The first condenser lens and first objective lens are positioned to observe a point on a first die position so that light entering the first objective lens passes through the first condenser lens, the transparent mask substrate and a point on the first die position. The second condenser lens and second objective lens are positioned to observe the corresponding point on a second die position so that light entering the second objective lens passes through the second condenser lens, the transparent mask substrate and the corresponding point of the second die position. The light exiting the first objective lens, after being shifted in phase by 180° by the phase adjustment unit, and the light exiting the second objective lens are both focussed on a split mirror. After being focussed on the split mirror the light is directed to a first detector and to a second detector. In this example the first detector is a photomultiplier tube and the second detector is a CCD imaging device.

The intensity, I, of the light at the first detector and the second detector is proportional to $\cos^2(\delta/2)$, where $\delta$ is the phase angle between light exiting the first objective lens at the split mirror and the light exiting the second objective lens at the split mirror. Since $\delta$ should be 180° the intensity, I, should be zero. Any deviation of I from zero indicates a defect in the mask. By moving the lenses the first die position and the second die position can be inspected in their entirety and any deviation of the first die position to the second die position will be detected. In this manner the entire mask can be inspected.

DESCRIPTION OF THE PREFERRED EMBODIMENTS

Figure 1:
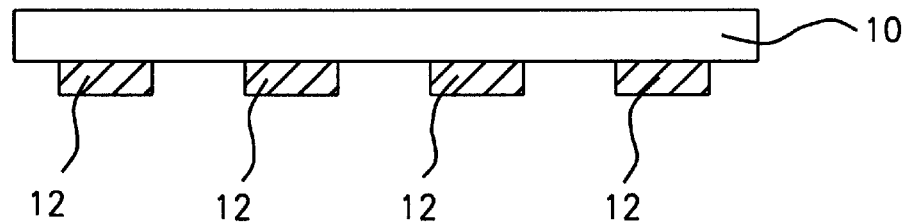
FIG. 1 shows a cross section of a binary mask.
Figure 2A:
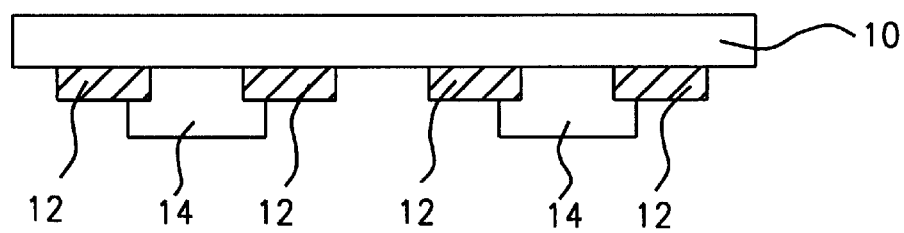
FIG. 2A shows a cross section of a Levenson type phase shifting mask.
Figure 2B:
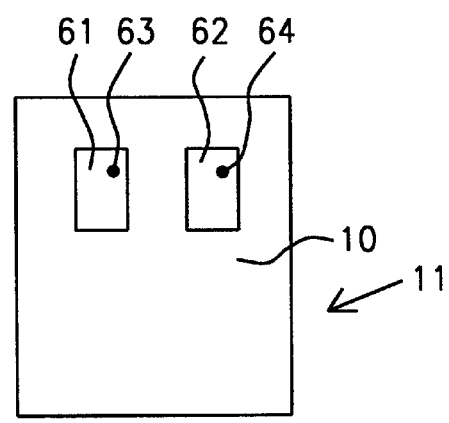
FIG. 2B shows a top view of a mask showing a first die position and a second die position.

Refer now to FIGS. 2A–5 for a description of the apparatus for inspecting masks of this invention. FIG. 2A shows a cross section of a Levenson type phase shifting mask having opaque mask elements 12 and transparent phase shifting elements 14 on a transparent mask substrate 10. FIG. 2B shows a mask 11 having a number of die positions on a transparent mask substrate 10. FIG. 2B shows a point 63 in a first die position 61 and a corresponding point 64 in an identical second die position 62.

Figure 3:
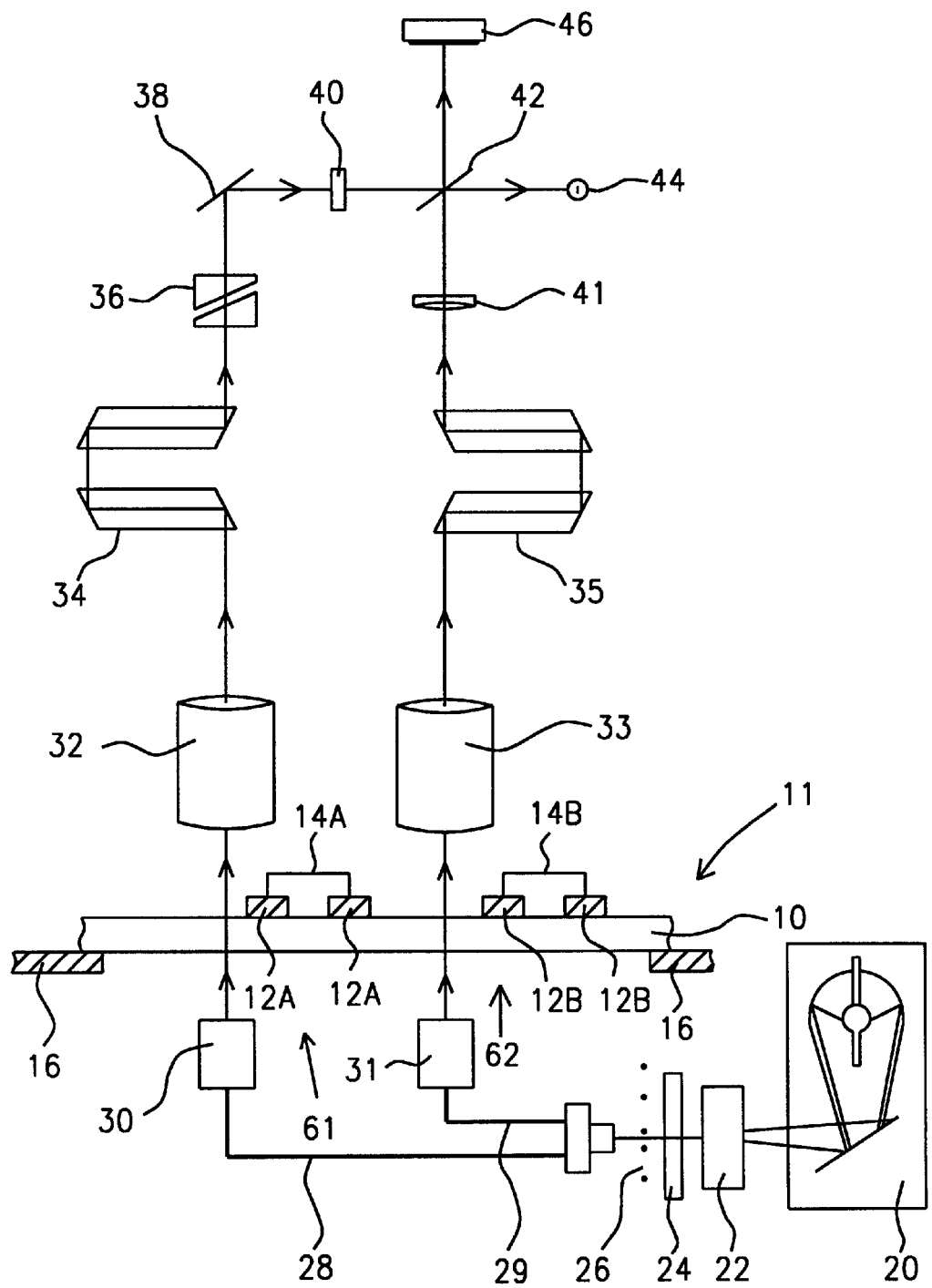
FIG. 3 shows a schematic view of the inspection apparatus of this invention in the calibration mode.
Figure 4:
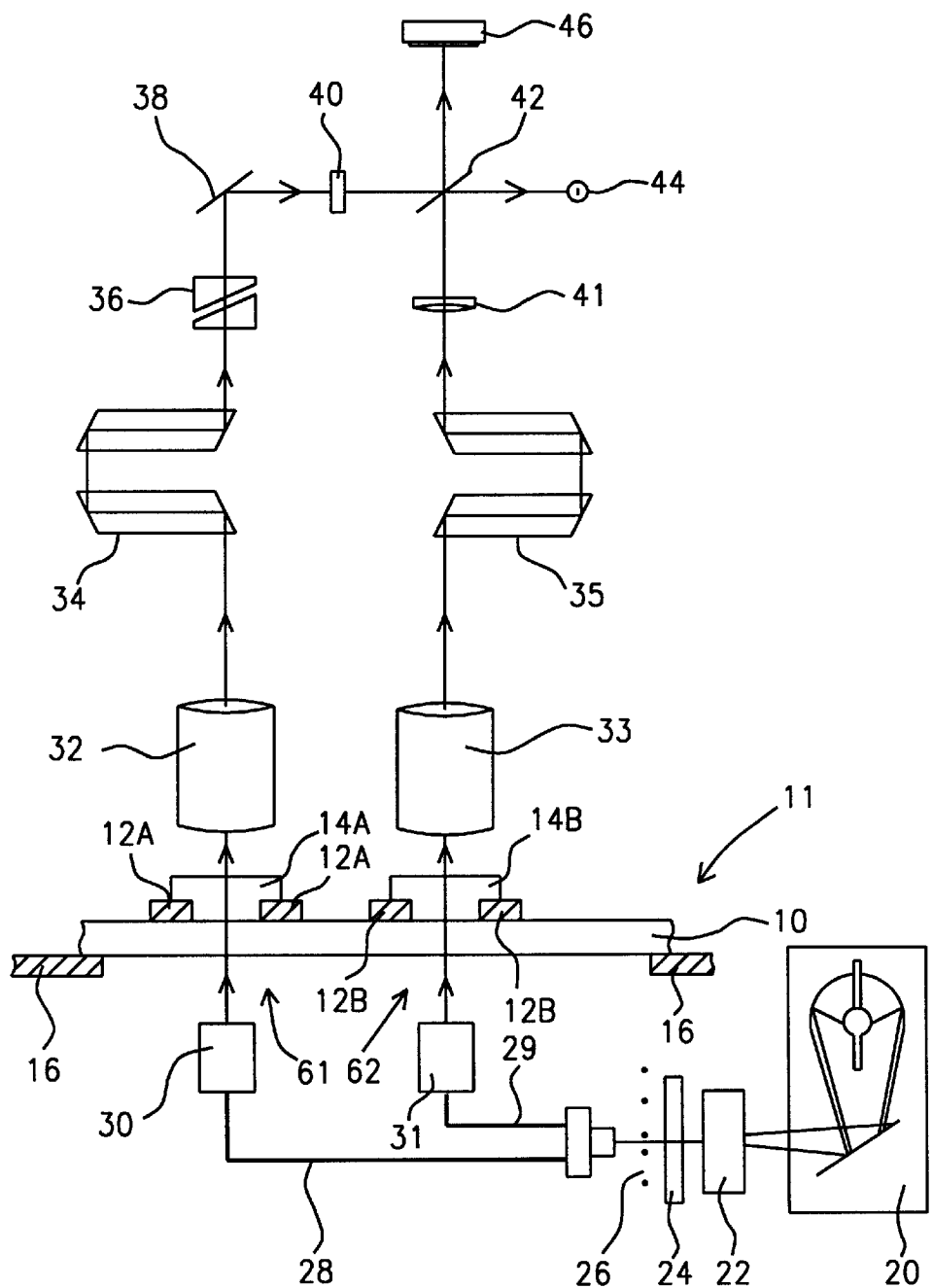
FIG. 4 shows a schematic view of the inspection apparatus of this invention in the inspection mode.

FIGS. 3 and 4 show schematic views of the apparatus of this invention for inspecting a mask 11 having phase shifting elements. The inspection is a die to die inspection and compares points on a first die position with corresponding points on a second die position. FIGS. 3 and 4 are the same except for the position of a first die position relative to the first condenser lens 30 and the first objective lens 32 and the position of a second die position relative to the second condenser lens 31 and the second objective lens 33. FIGS. 3 and 4 show a light source 20, in this example a He—Xe lamp. The light from the light source 20 passes through a homogenizer 22, a band pass filter 24, and a grating aperture 26 before illuminating a first fiber optic link 28 and a second fiber optic link 29. The light illuminating the fiber optic links 28 and 29 is monochromatic light and the first fiber optic link 28 and the second fiber optic link 29 are illuminated with the same intensity. The first fiber optic link 28 illuminates a first condenser lens 30 and the second fiber optic link 29 illuminates a second condenser lens 31. A first objective lens 32 is located directly above the first condenser lens 30. A second objective lens 33 is located directly above the first condenser lens 31.

A mask 11 is placed in a mask holder 16 and is located between the first and second condenser lenses, 30 and 31, and the first and second objective lenses, 32 and 33. The mask 11 has a transparent mask substrate 10, opaque mask elements 12A and 12B, and transparent phase shifting mask elements 14A and 14B. The mask 11, the first and second condenser lenses 30 and 31, and the first and second objective lenses 32 and 33 can be positioned relative to each other.

FIG. 3 shows the apparatus in calibration mode wherein the mask 11, the first condenser lens 30, the second condenser lens 31, the first objective lens 32, and the second objective lens 33 are positioned so that the light passing through the first condenser lens 30 into the first objective lens 32 passes through the transparent mask substrate 10 only and does not pass through phase shifting mask elements and the light passing through the second condenser lens 31 into the second objective lens 33 passes through the transparent mask substrate 10 only and does not pass through phase shifting mask elements. FIG. 4 shows the apparatus in inspection mode wherein the mask 11, the first condenser lens 30, the second condenser lens 31, the first objective lens 32, and the second objective lens 33 are positioned so that the light passing through the first condenser lens 30 into the first objective lens 32 passes through both the transparent mask substrate 10 and first phase shifting mask elements 14A at the first die position 61 and the light passing through the second condenser lens 31 into the second objective lens 33 passes through both the transparent mask substrate 10 and second phase shifting mask elements 14B at the second die position 62.

Figure 5:
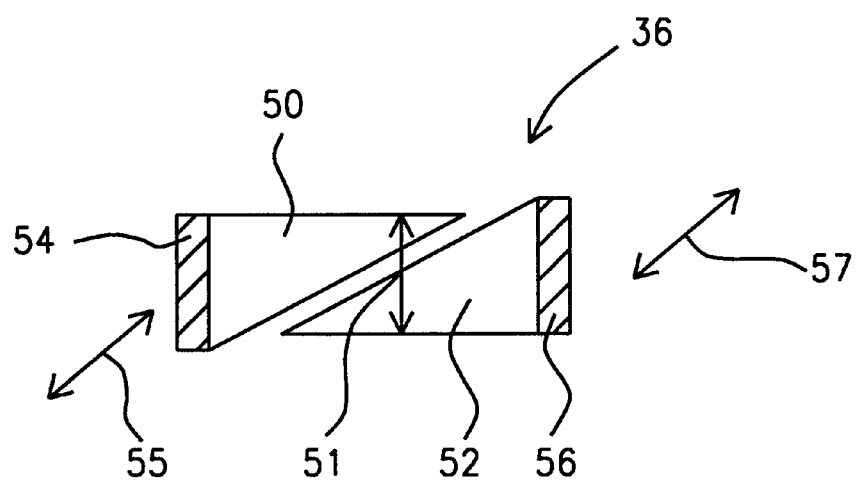
FIG. 5 shows a schematic view of the phase adjustment unit.

The light exiting the first objective lens 32 passes through a first parallel prism 34 into a phase adjustment unit 36. The detail of the phase adjustment unit 36 is shown in FIG. 5. The phase adjustment unit 36 provides phase shifting material of variable thickness. As shown in FIG. 5 the phase adjustment comprises a first triangular section 50 of phase shifting material and a second triangular section 52 of phase shifting material. The first triangular section 50 is attached to a first holder 55 and can be moved in the direction of the first arrow 55. The second triangular section 52 is attached to a second holder 56 and can be moved in the direction of the second arrow 57. By moving the first triangular section 50 and the second triangular section 52 the thickness 51 of phase shifting material the light will pass through, and thus the phase shift provided to the light, can be varied.

Returning again to FIGS. 3 and 4, the light exiting the phase adjustment unit 36 is reflected by a mirror 38, passes through a first shutter 40 and is focussed on a split mirror 42 by adjusting the first parallel prism 34. The light exiting the second objective lens 35 passes through a second parallel prism 35, a second shutter 41, and is focussed on the split mirror 42 by adjusting the second parallel prism 35. One half of the light from the first objective lens 32 passes through the split mirror 42 and is combined with one half of the light from second objective lens 33 reflected by the split mirror 42 and detected by the first detector 44. One half of the light from the first objective lens 32 is reflected by the split mirror 42 and is combined with one half of the light from second objective lens 33 passing through the split mirror 42 and detected by the second detector 46. In this example the first detector 44 is a photomultiplier tube 44 and the second detector 46 is a CCD imaging device.

The method of inspecting masks having phase shifting elements using the apparatus described above will now be described with reference to FIGS. 2A, 3, and 4. The method of this invention relies on the fact that the intensity of the light, I, reaching said the detector or the second detector is proportional to $\cos^2(\delta/2)$, where $\delta$ is the phase angle between the light from the phase adjustment unit 36 and the light from the second objective lens 33. When this phase angle is 180°, the intensity of the light reaching the first detector 44 or the second detector 46 is zero.

The apparatus is first calibrated by placing the apparatus in calibration mode, as shown in FIG. 3. In calibration mode the mask 11, the first condenser lens 30, the second condenser lens 31, the first objective lens 32, and the second objective lens 33 are positioned so that the light passing through the first condenser lens 30 into the first objective lens 32 passes through the transparent mask substrate 10 only and does not pass through phase shifting mask elements and the light passing through the second condenser lens 31 into the second objective lens 33 passes through the transparent mask substrate 10 only and does not pass through phase shifting mask elements. The phase adjustment unit 36 is then adjusted to reduce the light reaching the first detector or the light reaching the second detector to zero, or a minimum. This insures a 180° phase angle difference between the light exiting the phase adjustment unit 36 and the light exiting the second objective lens.

Without changing the adjustment of the phase adjustment unit the apparatus is placed in inspection mode as shown in FIG. 4. In inspection mode the mask 11, the first condenser lens 30, the second condenser lens 31, the first objective lens 32, and the second objective lens 33 are positioned so that the light passing through the first condenser lens 30 into the first objective lens 32 passes through both the transparent mask substrate 10 and first phase shifting mask elements 14A at the position of the first die 61 and the light passing through the second condenser lens 31 into the second objective lens 33 passes through both the transparent mask substrate 10 and second phase shifting mask elements 14B at the second die position 62. If the intensity of the light at the first detector or the second detector is not zero, or a minimum, the phase shift provided by the phase shifting elements seen by the first objective lens 32 and the second objective lens 33 are not equal and there is a defect in the mask. The first detector in this example is a photomultiplier tube providing a numerical reading. The second detector in this example is a CCD imaging device providing a visual display. The mask 11, first condenser lens 30, second condenser lens 31, first objective lens 32, and second objective lens 33 can be moved to scan the entire mask 11.

While the invention has been particularly shown and described with reference to the preferred embodiments thereof, it will be understood by those skilled in the art that various changes in form and details may be made without departing from the spirit and scope of the invention.

What is claimed is:

1. A method of inspecting masks having phase shifting elements, comprising the steps of:
   providing a mask having phase shifting mask elements formed on a transparent mask substrate at a number of die positions;
   providing a light source;
   providing a first objective lens and a second objective lens;
   holding said mask in a mask holder;
   providing a phase adjustment unit, wherein the phase shift of light passing through said phase adjustment unit can be varied;
   adjusting the phase of the light exiting said phase adjustment unit to provide a 180° phase shift;
   directing light from said light source through said transparent substrate and one of said phase shifting mask elements at a first said die position to said first objective lens;
   directing light from said first objective lens through said phase adjustment unit;
   directing light from said light source through said transparent mask substrate and one of said phase shifting mask elements at a second said die position to said second objective lens;
   combining the light exiting said phase adjustment unit and the light exiting said second objective lens at a first detector;
   combining the light exiting said phase adjustment unit and the light exiting said second objective lens at a second detector; and
   observing the intensity of said combined light at said first detector or the intensity of said combined light at said second detector.

2. The method of claim 1 wherein said light source comprises a Hg—Xe lamp, a homogenizer, a band pass filter, a grating aperture, a first fiber optic link, a second fiber optic link, a first condenser lens, and a second condenser lens.

3. The method of claim 1 wherein said first detector is a photomultiplier tube.

4. The method of claim 1 wherein said second detector is a CCD imaging device.

5. The method of claim 1 wherein said combining the light exiting said phase adjustment unit and the light exiting said second objective lens at a first detector and at a second detector uses a first parallel prism, a second parallel prism, and a mirror.

6. The method of claim 1 wherein said phase adjustment unit comprises a first triangular section of phase shifting material and a second triangular section of phase shifting material which can be moved relative to each other.

7. The method of claim 1 wherein the intensity of said combined light at said first detector or the intensity of said combined light at said second detector is proportional to the square of the cosine of one half of the phase angle between the light from said phase adjustment unit and the light from said second objective lens.

8. The method of claim 1 wherein said adjusting the phase of the light exiting said phase adjustment unit to provide a 180° phase shift further comprises:
   directing light from said light source through said transparent mask substrate without passing through any of said phase shifting mask elements to said first objective lens;
   directing light from said first objective lens through said phase adjustment unit;
   directing light from said light source through said transparent mask substrate without passing through any of said phase shifting mask elements to said second objective lens;
   combining the light exiting said phase adjustment unit and the light exiting said second objective lens at said first detector;
   combining the light exiting said phase adjustment unit and the light exiting said second objective lens at said second detector; and
   adjusting the phase adjustment unit until the intensity of the combined light at said first detector or said second detector is a minimum.

9. A method of inspecting masks having phase shifting elements, comprising the steps of:
   providing a mask comprising a transparent mask substrate and mask elements formed of phase shifting material at a number of die positions;
   providing a light source;
   providing a first condenser lens and a second condenser lens;
   providing a first objective lens and a second objective lens, wherein light entering said first objective lens first passes through said first condenser lens and light entering said second objective lens first passes through said second objective lens;
   holding said mask between said first objective lens and said first condenser lens and between said second objective lens and said second condenser lens;
   directing light from said light source to said first condenser lens and said second condenser lens;
   providing a phase adjustment unit, wherein the phase shift of light passing through said phase adjustment unit can be varied;
   passing the light exiting said first objective lens through said phase adjustment unit, thereby adjusting the phase of the light exiting said phase adjustment unit relative to the light exiting said second objective lens;
   combining the light exiting said phase adjustment unit and the light exiting said second objective lens at a first detector;
   combining the light exiting said phase adjustment unit and the light exiting said second objective lens at a second detector;

positioning said first objective lens and said second objective lens so that the light entering said first objective lens and said second objective lens passes through said transparent mask substrate but does not pass through said phase shifting mask elements;

adjusting the phase of the light exiting said first objective lens to provide a minimum light intensity at said first detector or said second detector;

positioning said first objective lens and said second objective lens, after adjusting the phase of the light exiting said first objective lens, so that the light entering said first objective lens passes through said transparent mask substrate and one of said phase shifting mask elements at a first said die position and the light entering said second objective lens passes through said transparent mask substrate and the corresponding said phase shifting mask elements at a second said die position; and observing the intensity of the light at said first detector or said second detector.

10. The method of claim 9 wherein said light source comprises a Hg—Xe lamp, a homogenizer, a band pass filter, and a grating aperture.

11. The method of claim 9 wherein said directing light from said light source to said first condenser lens and said second condenser lens uses a first fiber optic link and a second fiber optic link.

12. The method of claim 9 wherein said first detector is a photomultiplier tube.

13. The method of claim 9 wherein said second detector is a CCD imaging device.

14. The method of claim 9 wherein said combining the light exiting said phase adjustment unit and the light exiting said second objective lens at said first detector or at said second detector is accomplished using a first parallel prism, a second parallel prism, a mirror, and a split mirror.

15. The method of claim 9 wherein said phase adjustment unit comprises phase shifting material, wherein the thickness of said phase shifting material can be varied.

16. The method of claim 9 wherein the intensity of the combined light at said first detector or said second detector is proportional to the square of the cosine of one half of the phase angle between the light from said phase adjustment unit and the light from said second objective lens.

17. An apparatus for inspecting masks, comprising:

a light source;

a first condenser lens and a second condenser lens;

means to direct light from said light source to said first condenser lens;

means to direct light from said light source to said second condenser lens;

a first objective lens wherein light entering said first objective lens first passes through said first condenser lens;

a second objective lens wherein light entering said second objective lens first passes through said second condenser lens;

means for holding a mask between said first objective lens and said first condenser lens and between said second objective lens and said second condenser lens;

means for positioning said first objective lens and said first condenser lens;

means for positioning said second objective lens and said second condenser lens;

a phase adjustment unit, wherein said phase adjustment unit adjusts the phase of the light exiting said first objective lens relative to the light exiting said second objective lens;

means to combine the light exiting said phase adjustment unit and the light exiting said second objective lens;

a first detector positioned to detect the combined light exiting said phase adjustment unit and light exiting said second objective lens; and a second detector positioned to detect the combined light exiting said phase adjustment unit and light exiting said second objective lens.

18. The apparatus of claim 17 wherein said light source comprises a Hg—Xe lamp, a homogenizer, a band pass filter, and a grating aperture.

19. The apparatus of claim 17 wherein said means to direct light from said light source to said first condenser lens comprises a fiber optic link.

20. The apparatus of claim 17 wherein said means to direct light from said light source to said second condenser lens comprises a fiber optic link.

21. The apparatus of claim 17 wherein said first detector is a photomultiplier tube.

22. The apparatus of claim 17 wherein said second detector is a CCD imaging device.

23. The apparatus of claim 17 wherein said means to combine the light exiting said phase adjustment unit and the light exiting said second objective lens comprises a first parallel prism, a second parallel prism, a split mirror, and a mirror.

24. The apparatus of claim 17 wherein said phase adjustment unit comprises a first triangular section of phase shifting material and a second triangular section of phase shifting material which can be moved relative to each other.

* * * * *